(12) United States Patent
Lai

(10) Patent No.: US 9,125,635 B2
(45) Date of Patent: Sep. 8, 2015

(54) SAMPLING DEVICE FOR VAGINAL SPECIMEN

(76) Inventor: Hung-Cheng Lai, Taipei (TW)

( * ) Notice: Subject to any disclaimer, the term of this patent is extended or adjusted under 35 U.S.C. 154(b) by 819 days.

(21) Appl. No.: 12/989,486

(22) PCT Filed: Feb. 3, 2009

(86) PCT No.: PCT/CN2009/000126
§ 371 (c)(1),
(2), (4) Date: Dec. 21, 2010

(87) PCT Pub. No.: WO2009/132505
PCT Pub. Date: Nov. 5, 2009

(65) Prior Publication Data
US 2011/0105953 A1 May 5, 2011

(30) Foreign Application Priority Data
Apr. 28, 2008 (CN) .......................... 2008 1 0094330

(51) Int. Cl.
*A61B 5/00* (2006.01)
*A61B 10/02* (2006.01)
*A61B 10/00* (2006.01)
*A61B 17/22* (2006.01)

(52) U.S. Cl.
CPC ............. *A61B 10/02* (2013.01); *A61B 10/0045* (2013.01); *A61B 10/0291* (2013.01); *A61B 2010/0074* (2013.01); *A61B 2017/22082* (2013.01)

(58) Field of Classification Search
CPC ............... A61B 10/0045; A61B 10/02; A61B 2017/22082
USPC ................ 600/573, 581, 562, 569, 572, 563; 435/5
See application file for complete search history.

(56) References Cited

U.S. PATENT DOCUMENTS

| | | | | | |
|---|---|---|---|---|---|
| 3,057,352 | A | * | 10/1962 | McKenna | 604/204 |
| 3,254,647 | A | * | 6/1966 | Vogel | 604/85 |
| 4,151,831 | A | * | 5/1979 | Lester | 600/549 |
| 4,256,107 | A | * | 3/1981 | White | 604/248 |
| 6,551,279 | B1 | * | 4/2003 | Hyun | 604/132 |
| 2003/0023189 | A1 | * | 1/2003 | Kuo | 600/584 |
| 2004/0152206 | A1 | * | 8/2004 | Davis et al. | 436/514 |
| 2004/0158188 | A1 | * | 8/2004 | Kauffmann et al. | 604/1 |
| 2006/0287610 | A1 | * | 12/2006 | Wiegerinck et al. | 600/563 |
| 2007/0255167 | A1 | * | 11/2007 | Christensen et al. | 600/561 |
| 2008/0071190 | A1 | * | 3/2008 | Gorodeski et al. | 600/551 |
| 2009/0062715 | A1 | * | 3/2009 | Saunders et al. | 604/1 |
| 2011/0004122 | A1 | * | 1/2011 | Sangha | 600/572 |
| 2011/0087133 | A1 | * | 4/2011 | Ching et al. | 600/572 |
| 2011/0144534 | A1 | * | 6/2011 | Gombrich | 600/572 |
| 2012/0009588 | A1 | * | 1/2012 | Rajagopal et al. | 435/6.15 |

* cited by examiner

*Primary Examiner* — Sean Dougherty
*Assistant Examiner* — Michael C Stout
(74) *Attorney, Agent, or Firm* — Rosenberg, Klein & Lee

(57) ABSTRACT

A sampling device for vaginal specimens is revealed. The sampling device for vaginal specimens includes a tubular unit whose one end is disposed with a sampling unit, and at least one hole arranged on side walls of the same end of the tubular unit. The other end of the tubular unit is disposed with a saclike body or is inserted with an injection unit so as to send solution through the tubular unit to the hole for flushing vagina. By the sampling unit, a flushed vaginal specimen is collected. Thus the collection procedures of the specimen are easy and convenient to be performed and users have no uncomfortable feelings due to the lubricant solution.

9 Claims, 13 Drawing Sheets

SAMPLING DEVICE FOR VAGINAL SPECIMEN

BACKGROUND OF THE INVENTION

1. Field of the Invention

The present invention relates to a sampling device, especially to a sampling device for collecting vaginal specimens with excellent convenience and accuracy of self-sampling.

2. Description of Related Art

Nowadays awareness on various women's issues is aroused and women pay more attentions on the health care and financial planning. As to women's health care, pap smears and venereal disease tests are important for women. While being checked and collected specimens for these tests by doctors in hospitals or clinics, most of women feel uncomfortable and embarrassing. Although Pap Smear Screening has been promoted as an important medical test, still a lot of women are unwilling to get regular check-ups. Needless to say, women in undeveloped or developing countries have infrequent or no pap smear screening. Besides smear tests, molecular diagnostics technologies herald a new era for cervical cancer screening due to progress in molecular diagnostic markers for various pathogens such as human papilloma virus (HPV). The tests combine self-sampling process with molecular biomarkers have become important screening tools for cervical cancer and sexually transmitted diseases. Thus a self-sampling device has been developed for women to collect specimens for molecular diagnostic tests by themselves.

Refer to FIG. 1, a schematic drawing of an embodiment of a conventional sampling device for vaginal specimens is revealed. As shown in figure, a sampling device for vaginal specimens 10 consists of a tube 12, a push rod 14 and a sampling member 16. A sampling opening 122 is on a front end of the tube 12 while the push rod 14 is inserted inside the tube 12 and is extended out of a rear end of the tube 12. A clipping member 142 is arranged on the front end of the push rod 14 and is inside the tube 12. The clipping member 142 clips and holds the sampling member 16 and the sampling member 16 is mounted inside the sampling opening 122. During sampling processes, women insert the tube 12 into the vagina and push the push rod 14 so as to make the clipping member 142 drive the sampling member 16. Thus the sampling member 16 moves forward and exposes outside the sampling opening 122 to collect specimens (such as cell membranes and tissue fluid). By the sampling member 16, the sampling device for vaginal specimens 10 collects the samples directly and the vagina or the sampling member 16 was not lubricated in advance. This leads to discomfort of women during sampling processes. Thus a sampling way for collecting specimens by drawing the solution has been developed.

Refer to FIG. 2, another embodiment of a conventional sampling device for vaginal specimens is disclosed. A sampling device for vaginal specimens 20 includes a tube 22 and a push rod 24. A sampling opening 222 and an injection opening 224 are disposed on a front end of the tube 22. A holding (handle) portion 226 is arranged on a wall of a rear end of the tube 22. The push rod 24 is inserted into and is arranged slidingly inside the tube 22. A piston 242 is disposed on a front end of the push rod 24 for injecting/drawing solution. During collecting processes of specimens, women insert the tube 22 into the vagina and push the push rod 24 to drive the piston 242 move and the solution therefront moves toward the injection opening 224 (or the sampling opening 222) to be injected into the vagina. Then pull the push rod 24 to draw the solution through the sampling opening 222 (or the injection opening 224) for collecting specimens. The sampling is achieved by pushing the push rod 24 to inject the solution for washing area to be sampled. Then pull the push rod 24 to draw the sampling solution. However, such operation is neither convenient nor easy. And drawing effect of the push rod 24 being pulled is uncertain and unstable. This causes troubles in following medical tests so that this sampling way is not so ideal.

Moreover, because lives of modern people are so busy, people don't have time to go to hospitals or clinics for medical tests regularly. Once people can buy sampling device for specimens at convenience stores, collect the specimens by themselves at home and send the collected specimens to the hospitals or medical test laboratories for following test procedures, screening tests of gynecologic diseases are going to be more easier and prevalent. Furthermore, for women that live in mountain range or other area lack of medical sources, or those who are traditional and conservative, such self-sampling procedure is quite convenient and is beneficial to women's health.

Thus there is a need to provide a new sampling device for vaginal specimens that not only improves shortcomings of conventional sampling devices such as no lubricants and poor sampling effect, but also prevents women from feeling uncomfortable and maladapted during sampling processes. Moreover, the sampling device has a special design that enables the device to be delivered more conveniently.

SUMMARY OF THE INVENTION

Therefore it is a primary object of the present invention to provide a sampling device for vaginal specimens in which the vagina is flushed with solution and a sample is collected from the vagina by a sampling member so as to avoid discomfort caused by vaginal dryness.

It is another object of the present invention to provide a sampling device for vaginal specimens that is convenient for users to collect vaginal specimens by themselves and is designed with an easy delivery member so that tests for gynecologic diseases are going to be more prevalent.

It is another object of the present invention to provide a sampling device for vaginal specimens that combines with scraping operation so as to improve sampling accuracy and efficiency.

In order to achieve above objects, a sampling device for vaginal specimens according to the present invention consists of a tubular unit, a sampling unit and a saclike body. The front end of the tubular unit is disposed with at least one hole and a flow channel is mounted in the tubular unit, connecting with the hole. The sampling unit is arranged on the front end of the tubular unit while the saclike body is connected with a rear end of the tubular unit. The saclike body is disposed with a pour opening that connects with the flow channel.

Another embodiment of the sampling device for vaginal specimens of the present invention includes a tubular unit, a sampling unit and an injection rod. The front end of the tubular unit is disposed with at least one hole and a flow channel is mounted in the tubular unit, connecting with the hole. The sampling unit is arranged on the front end of the tubular unit. The injection rod is inserted in the flow channel of the tubular unit and a piston is disposed on a front end of the injection rod.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
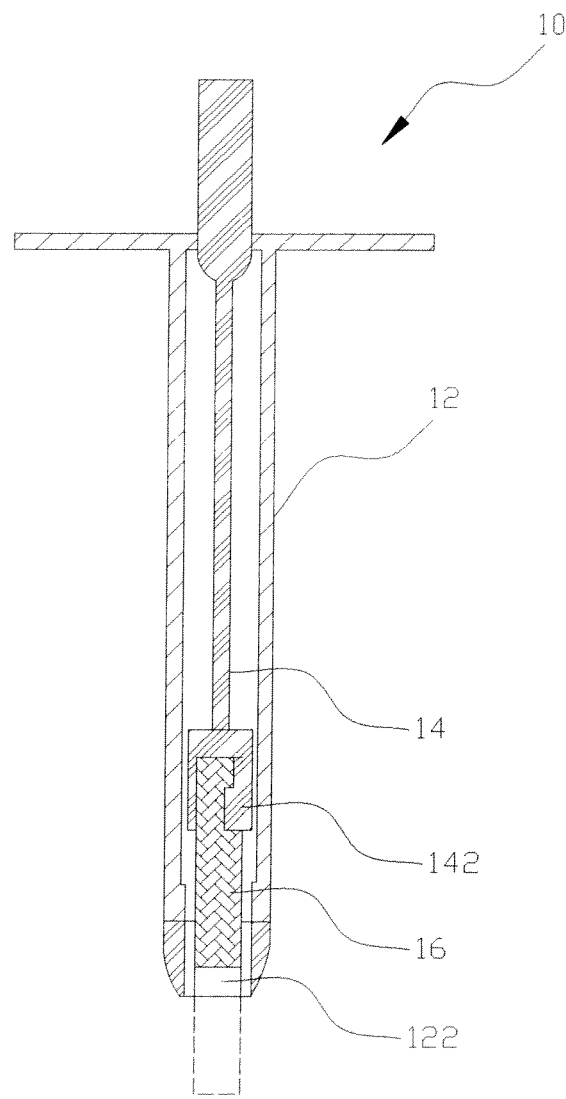
FIG. 1 is a schematic drawing showing an embodiment of a conventional sampling device for vaginal specimens.
Figure 2:
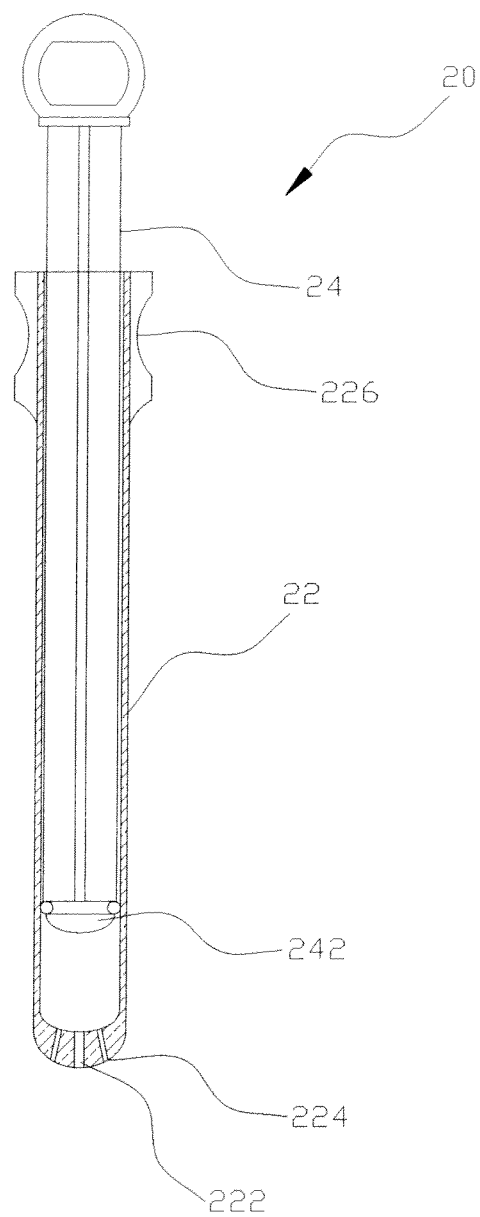
FIG. 2 is a schematic drawing showing another embodiment of a conventional sampling device for vaginal specimens.
Figure 3:
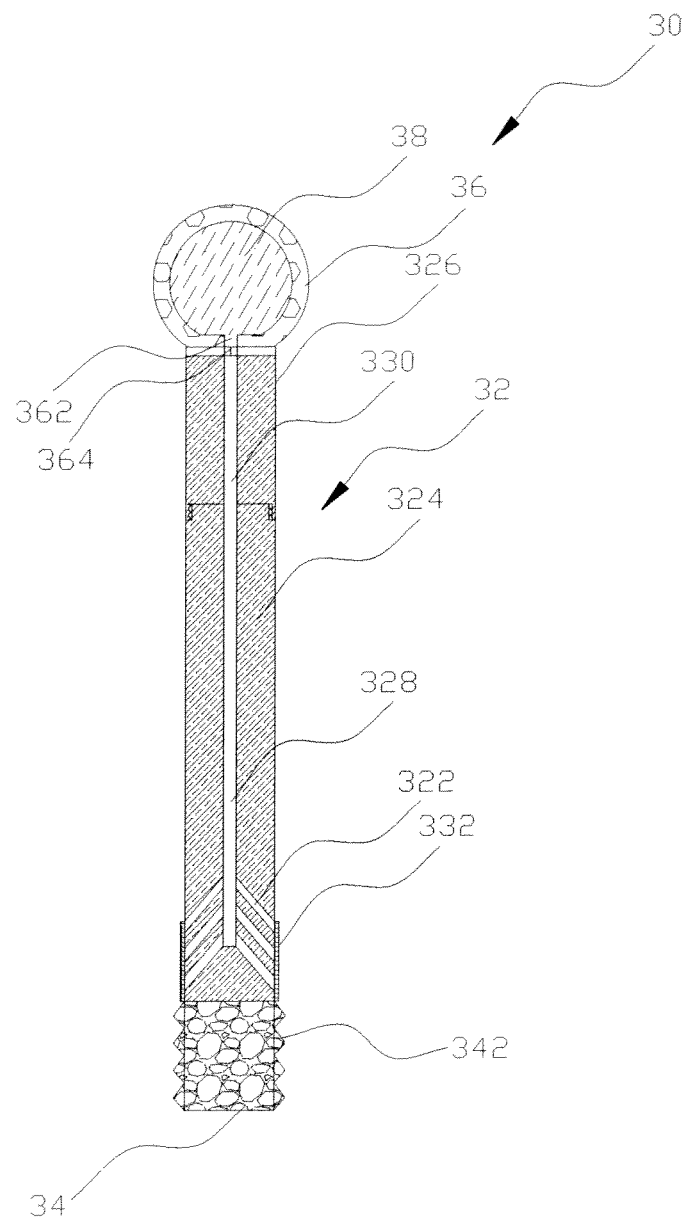
FIG. 3A is a schematic drawing showing a first embodiment of a sampling device for vaginal specimens according to the present invention.
FIG. 3B is a schematic drawing showing operation of the first embodiment in according to the present invention.
FIG. 3C is a schematic drawing showing packaging of the first embodiment according to the present invention.

Refer to FIG. 3A, a schematic drawing showing an embodiment of a sampling device for vaginal specimens of the present invention is disclosed. A sampling device for vaginal specimens 30 according to the present invention includes a tubular unit 32, a sampling unit 34 and a saclike body 36. The sampling unit 34 is disposed on one end (front end) of the tubular unit 32 and is an absorptive member (such as sponge) in this embodiment. A plurality of holes 322 is arranged on side walls of the front end of the tubular unit 32. In a preferred embodiment, the hole 322 is an opening for flow channel that slopes downward and a hole film 332 is sealed over the hole 322. The tubular unit 32 further consists of a first tubular member 324 on the front end thereof and a second tubular member 326 on the rear end thereof. The second tubular member 326 is connected with the first tubular member 324 by threads. A first flow channel 328 is mounted inside the first tubular member 324 for being connected with the hole 322 and a second flow channel 330 is mounted inside the second tubular member 326 that connects with the first flow channel 328. Generally, the first flow channel 328 and the second flow channel 330 are respectively formed on partial area of an inner wall of the first tubular member 324 and the second tubular member 326. The first flow channel 328 together with the second flow channel 330 form a flow channel inside the tubular unit 32. The saclike body 36 is connected with the rear end of the tubular unit 32. That means the saclike body 36 is joined with the second tubular member 326. In this embodiment, the saclike body 36 is pivoted or threaded with the second tubular member 326 and is filled with solution 38 (such as water or other liquid). A pour opening 362 is arranged on the saclike body 36 and is connected with the second flow channel 330. The saclike body 36 is with certain hardness or support strength so that it will not easily get compressed by a light contact. Moreover, the saclike body 36 can also have certain elasticity. Furthermore, a membrane 364 is disposed on the pour opening 362 or between the pour opening 362 and the second flow channel 330 so as to block the liquid 38 inside the saclike body 36 temporarily. The membrane 364 can be a stop valve. In addition, the above first flow channel 328 and second flow channel 330 can be formed by direct disposition of a tube (not shown in figure). The tube is connected with the pour opening 362 and the front end of the tube is connected with the hole 322.

Figure 3B:
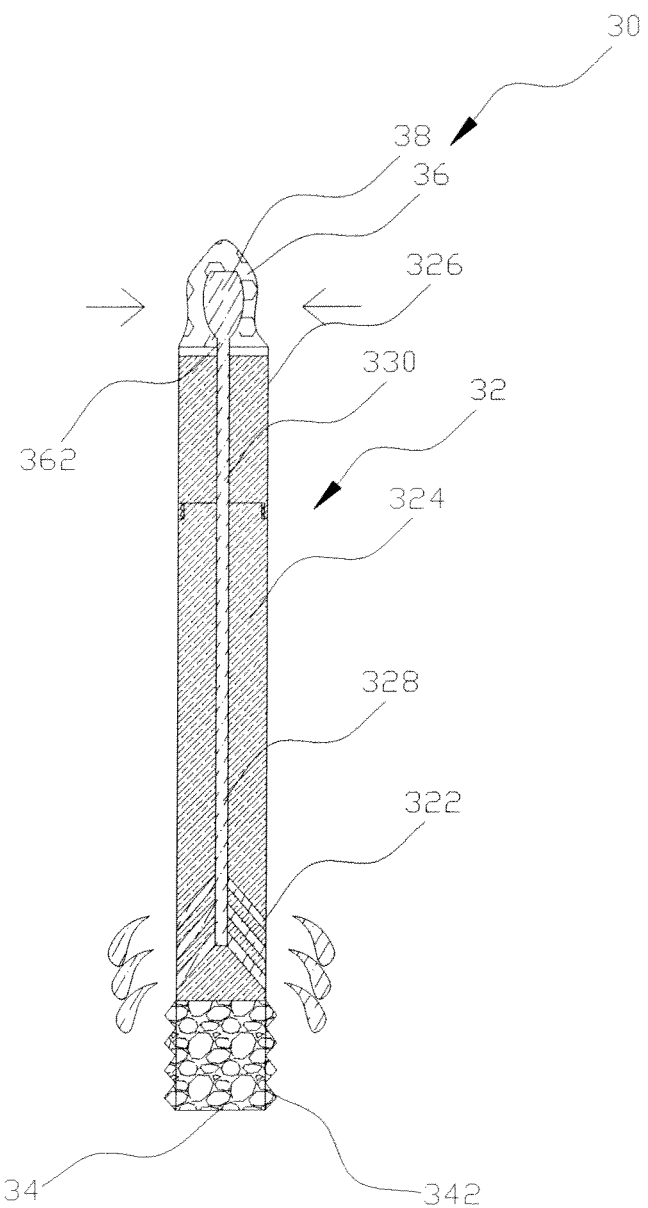
Figure 3C:
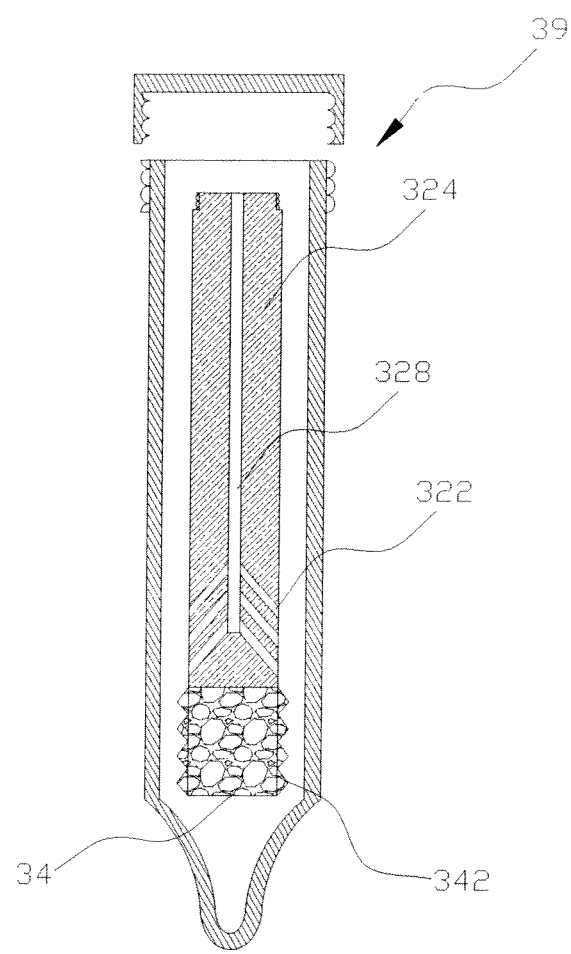

Refer to FIG. 3B, while sampling, the user inserts the tubular unit 32 into the vagina (not shown in figure) firstly. Then the saclike body 36 is squeezed so that the liquid 38 therein flows over the membrane 364 (or the stop valve), enters the second flow channel 330, through the first flow channel 328, and flows over the hole film 332 to be injected into the vagina for flushing the vagina. The sampling unit 34 is used to absorb the flushing liquid containing released cells and tissue fluid) to obtain specimens. After finishing sampling, the tubular unit 32 is disassemble into the first tubular member 324 and the second tubular member 326. Finally, the first tubular member 324 with the sampling unit 34 is sent to medical institutions to be tested. Moreover, the sampling unit 34 is further disposed with a plurality of scraping members 342 such as convex surfaces, protrusions or other projecting objects so as to increase scraping efficiency of cells and tissue fluid. Furthermore, for safety sake, the sampling unit 34 is fastened and connected with one end of a drawing string (not shown in figure) that extends through the tubular unit 32 while the other end of the drawing string is located on a certain position of the sampling device for vaginal specimens 30. Once the sampling unit 34 falls off, it can be drawn out by the drawing string. In addition, for convenience of taking the following test procedures, the disassembled first tubular member 324 (together with the sampling unit 34) can be packaged and sealed in a centrifuge tube 39, as shown in FIG. 3C. Thus the centrifuge tube 39 is delivered to the medical institutions to be tested and the user just needs to wait for test results. Therefore, users can overcome limits of time, space, or privacy. And the device also improves diagnosis and treatment for gynecologic diseases as well as prevalence and convenience of medical tests.

In a word, the discomfort of the area being sampled caused by friction of the sampling unit 34 is reduced by flushing of the solution 38. At the same time, the solution 38 also increases the connection between the sampling unit 34 and the cells/tissue fluid. By means of simple operation of the present invention, women can collect vaginal specimens by themselves in an easy and relaxing manner. Moreover, the accuracy of the specimens to be tested is increased.

Figure 4A:
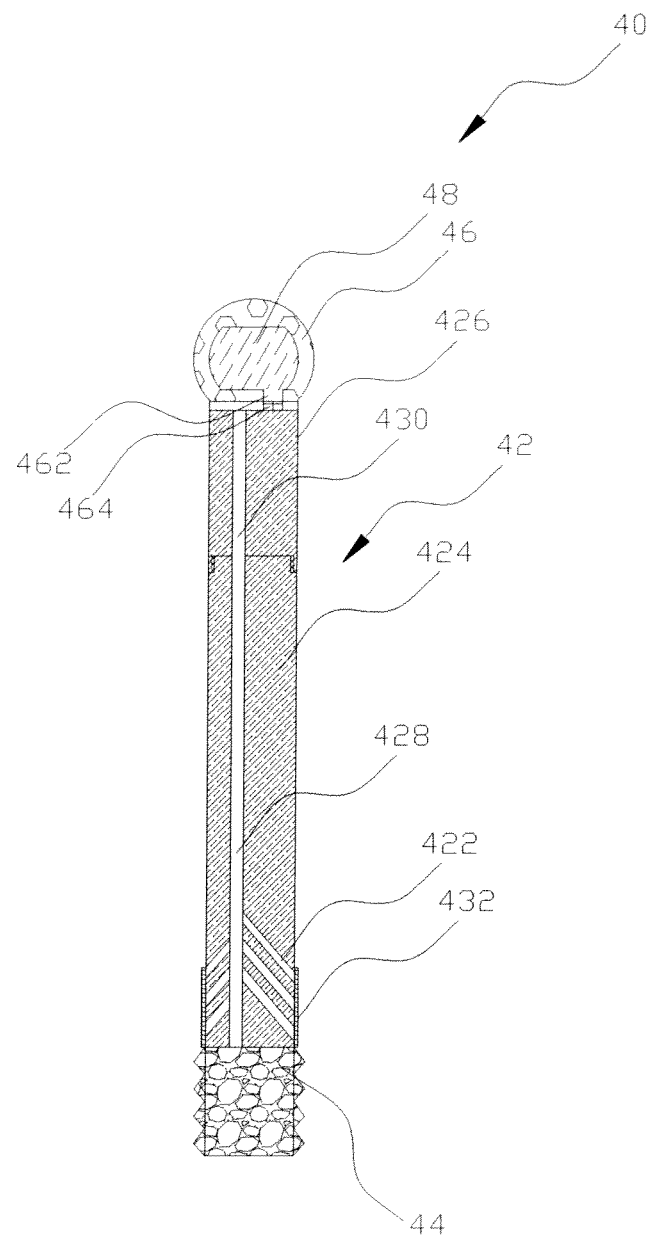
FIG. 4A is a schematic drawing showing another embodiment of a sampling device for vaginal specimens according to the present invention.

Refer to FIG. 4A, a schematic drawing of another embodiment is revealed. A first flow channel 428 and a second flow channel 430 of a tubular unit 42 are moved closer to one side of the device so that a pour opening 462 of a saclike body 46 and the second flow channel 430 are staggered and disconnected. A sampling device for vaginal specimens 40 of the present invention includes a first tubular member 424 disposed with at least one hole 422 and a first flow channel 428, and a second tubular member 426 arranged with a second flow channel 430. A sampling unit 44 is disposed on a front end of the first tubular unit 424 while a rear end of the first tubular unit 424 is treaded with the second tubular member 426. The saclike body 46 is pivoted on a rear end of the second tubular member 426 of the tubular unit 42 so that the saclike body 46 can be rotated pivotedly. A solution 48 is filled in the saclike body 46. In this embodiment, before use the pour opening 462 and the second flow channel 430 are staggered so as to prevent leaking of the solution 48. Moreover, a membrane 464 is disposed on the pour opening 462 or between the pour opening 462 and the second flow channel 430 while a hole film 432 is sealed over the hole 422 so as to avoid leaking of the liquid 48 in use.

Figure 4B:
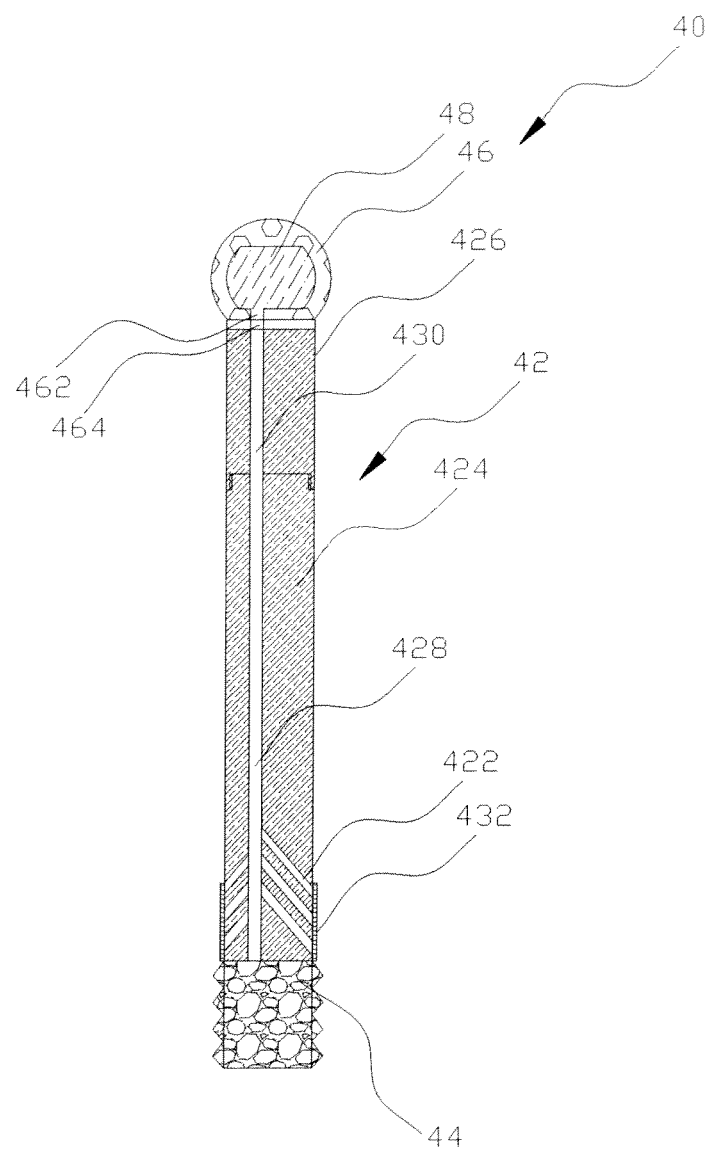
FIG. 4B is a schematic drawing showing the embodiment in FIG. 4A after being rotated according to the present invention.
Figure 4C:
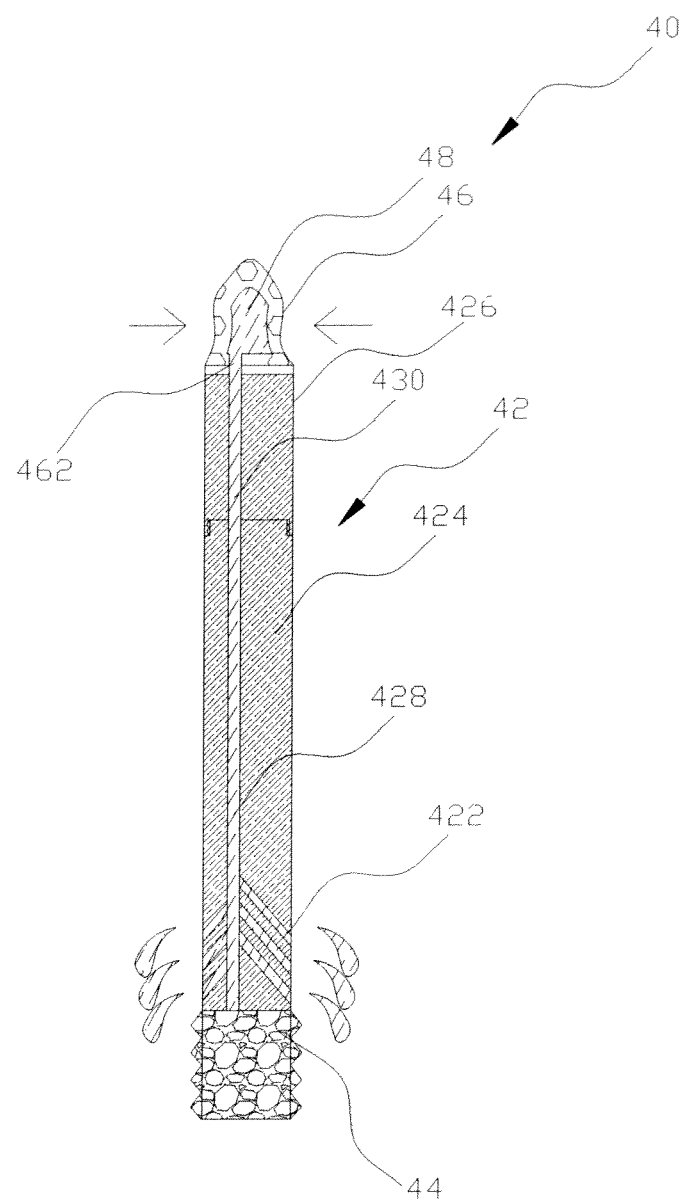
FIG. 4C is a schematic drawing showing the embodiment in FIG. 4A while injecting solution according to the present invention.

With reference of FIG. 4B, while applying the sampling device for vaginal specimens 40, the tubular unit 42 is inserted into the vagina and then rotate the saclike body 46 (or the tubular unit 42) so as to make the pour opening 462 and the second flow channel 430 correspond to and connect with each other. Also refer to FIG. 4C, the saclike body 46 is squeezed so that the liquid 8 flows over the membrane 464, enters the second flow channel 430, through the first flow channel 428, and flows over the hole film 432 to be sent outside the hole 422 and injected into the vagina for lubrication. Through the solution 48 working as lubricant for vagina, the uncomfortable feelings of women generated during collection processes of specimens can be avoided. Furthermore, the first tubular unit 424 is threaded with the second tubular unit 426. Thus after specimen collection, women can disassemble the first tubular unit 424 with the sampling unit 44 and sent it to test labs. Therefore, there is no need to go to gyniatrics clinics for smear tests.

Figure 5A:
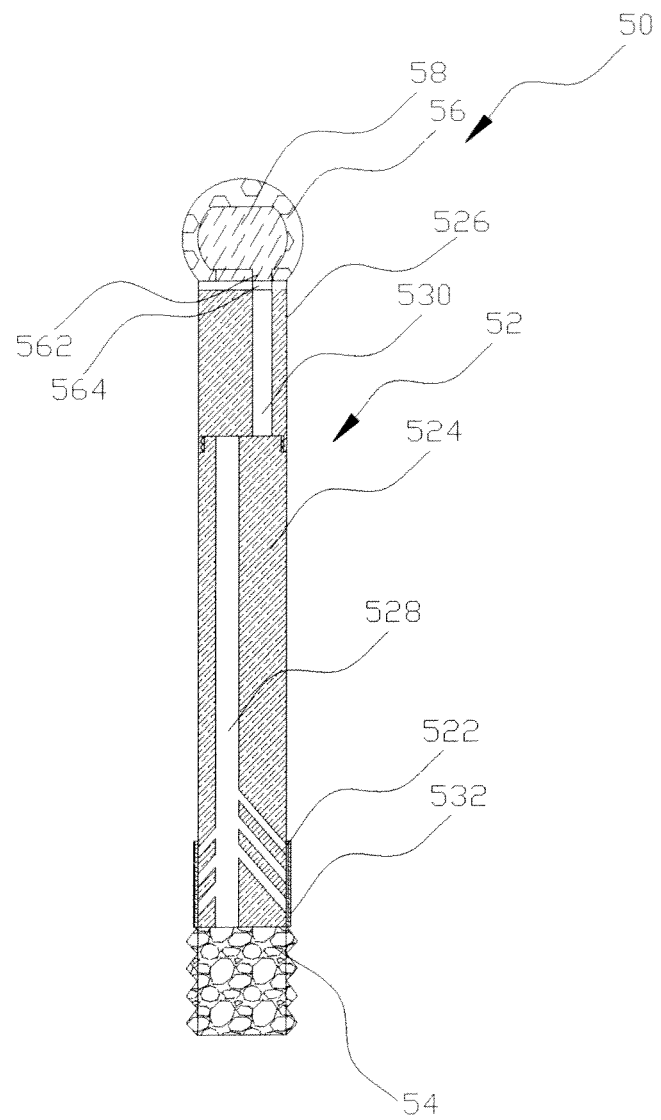
FIG. 5A is a schematic drawing showing a further embodiment of a sampling device for vaginal specimens according to the present invention.

Refer to FIG. 5A, a schematic drawing showing a further embodiment according to the present invention is revealed. A first flow channel 528 and a second flow channel 530 of a tubular unit 52 of a sampling device for vaginal specimens 50 are staggered. The tubular unit 52 is also disposed with at least one hole 522, a first tubular member 524, a second tubular member 526, the first flow channel 528, the second flow channel 530 and a hole film 532. The hole 522 is arranged on one end of the first tubular member 524 and the hole film 532 covers the hole 522 while the first flow channel 528 is mounted in the first tubular member 524 and the second flow channel 530 is disposed in the second tubular member 526. The rear end of the first tubular member 524 is pivoted (or threaded) with the second tubular member 526 and a sampling unit 54 is disposed on a front end of the first tubular unit 524. A saclike body 56 filled with solution 58 is pivoted on a rear end of the second tubular member 526 and a pour opening 562 of the saclike body 56 is connected with the second flow channel 530. And a membrane 564 is disposed on the pour opening 562 or between the pour opening 562 and the second flow channel 530.

Figure 5B:
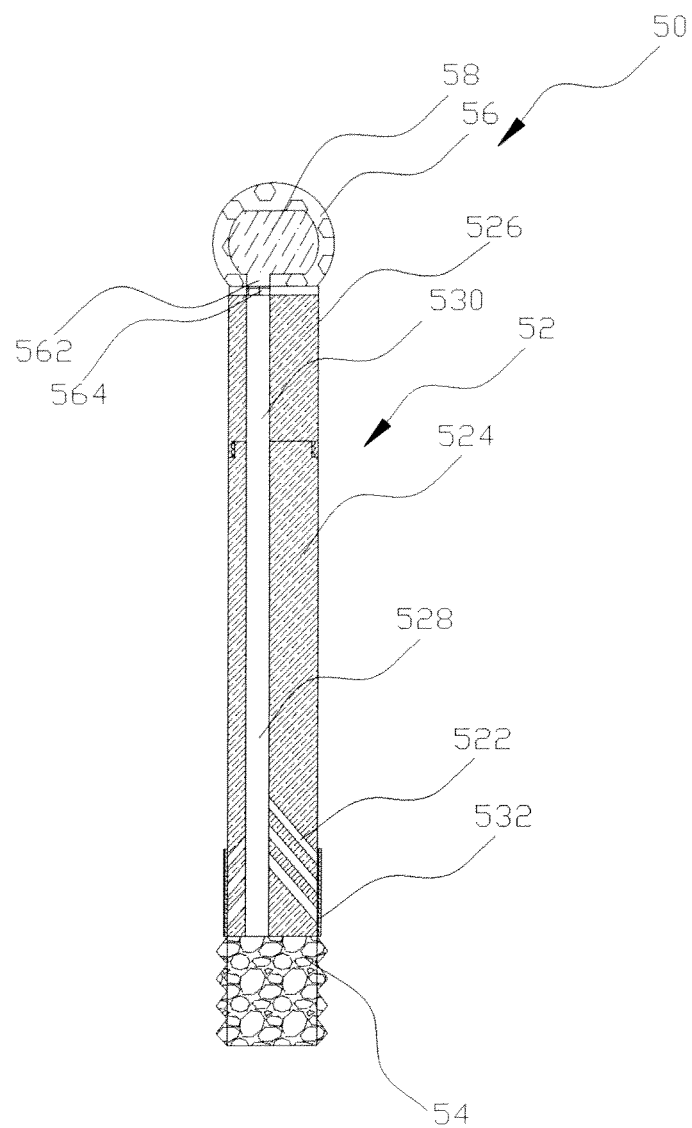
FIG. 5B is a schematic drawing showing the embodiment IN FIG. 5A after being rotated according to the present invention.
Figure 5C:
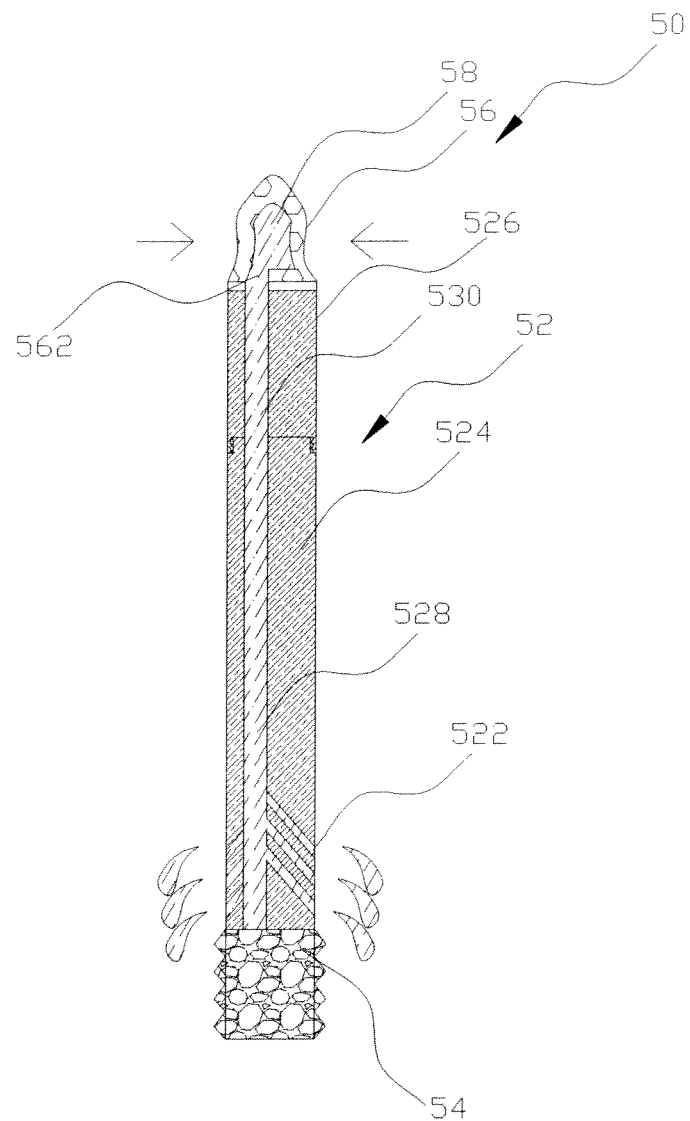
FIG. 5C is a schematic drawing showing the embodiment IN FIG. 5A while injecting solution according to the present invention.

Before use, as shown in FIG. 5B, the tubular unit 52 is inserted into the vagina and rotate the first tubular member 52 (or the second tubular member 526) so as to make the first flow channel 528 and the second flow channel 530 connect with each other correspondingly. Then as shown in FIG. 5C, the saclike body 56 is squeezed and the solution 58 passes through the second flow channel 530, the first flow channel 528, flowing out of the hole 522. During the processes, the membrane 564 and the hole film 532 are broken so that the solution 58 is injected into the vagina through the hole 522. The sampling unit 54 is used to collect specimens from the lubricated vagina. This helps women avoid discomfort caused by the sampling processes.

Figure 6A:
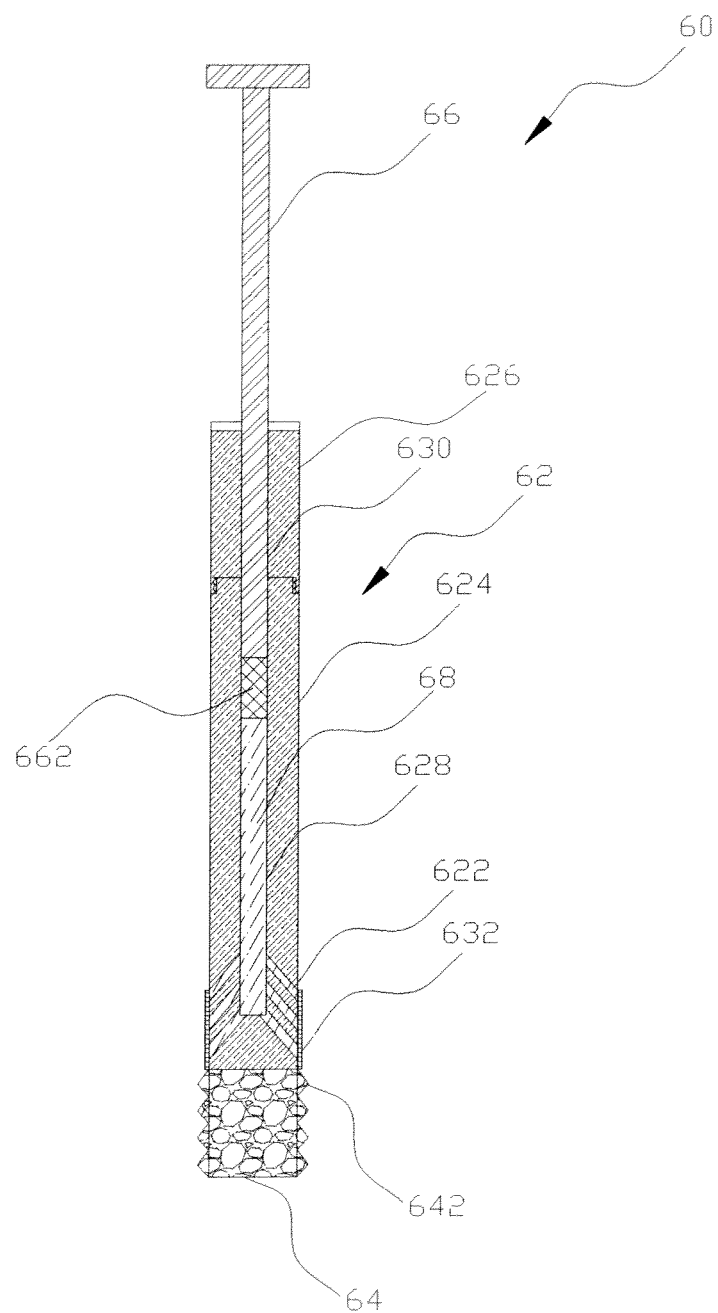
FIG. 6A is a schematic drawing showing a further embodiment of a sampling device for vaginal specimens according to the present invention.

Refer to FIG. 6A, a further embodiment of the present invention is disclosed. A sampling device for vaginal specimens 60 according to the present invention is composed of a tubular unit 62, a sampling unit 64 and an injection rod 66. The tubular unit 62 is also disposed with at least one hole 622, a first tubular member 624, a second tubular member 626, a first flow channel 628, and a second flow channel 630. The hole 622 is arranged on a front end (such as side wall) of the first tubular member 624. The first flow channel 628 is disposed in the first tubular member 624 and the second flow channel 630 is mounted in the second tubular member 626. The first tubular member 624 is threaded with the second tubular member 626 and the first flow channel 628 is connected with the second flow channel 630 correspondingly. The first flow channel 628 together with the second flow channel 630 form a flow channel inside the tubular unit 62. A sampling unit 6L is disposed on a front end of the first tubular member 624 and is an absorptive member (such as sponge). Moreover, the sampling unit 64 is further disposed with a plurality of scraping members 642 such as convex surfaces, protrusions or other projecting objects so as to increase scraping efficiency of cells and tissue fluid. The injection rod 66 is inserted into the second flow channel 630 of the second tubular member 626 and is moved slidingly inside the first flow channel 628 and the second flow channel 630. A piston 662 is disposed on one end of the injection rod 66 that also moves slidingly in the first flow channel 628 and the second flow channel 630. A loading space between the piston 662 and the hole 622 is filled with solution 68. Generally, the loading space is the first flow channel 628, or further including the second flow channel 630. Moreover, the hole 622 is covered by a hole film 632 so as to avoid the solution 68 flowing out of the hole 622.

Figure 6B:
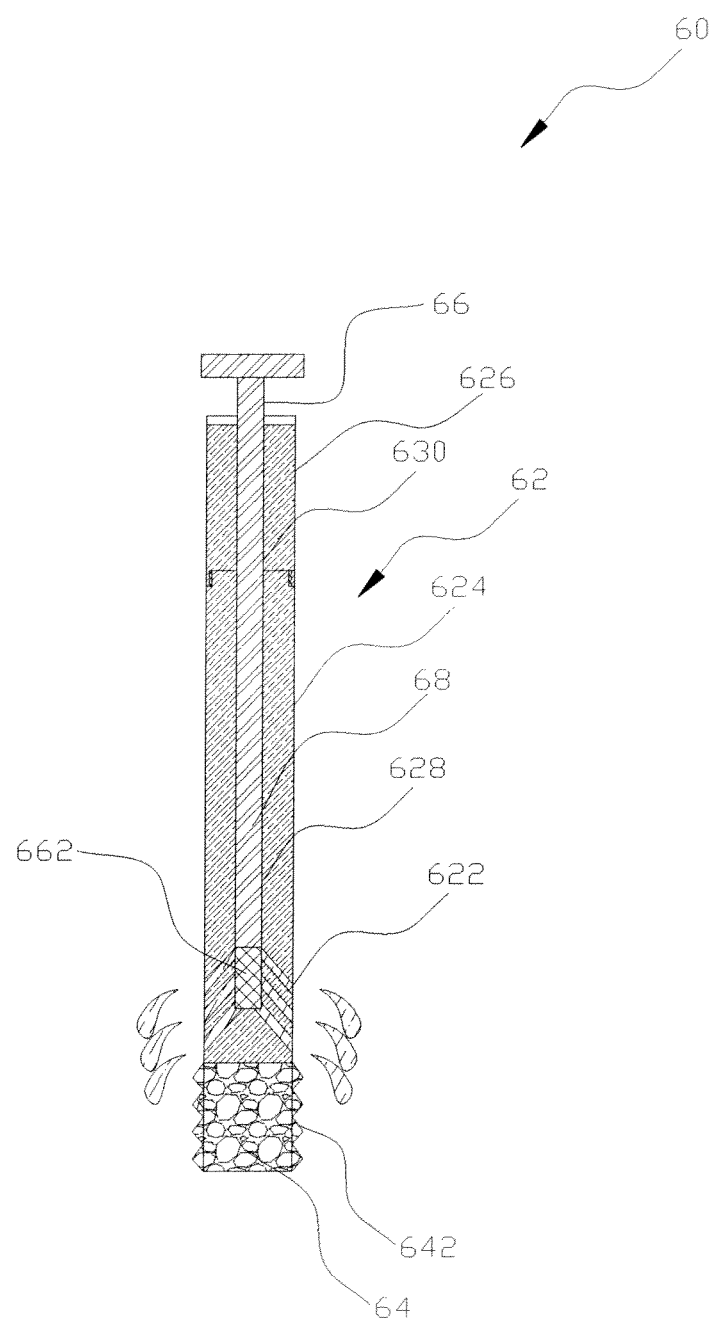
FIG. 6B is a schematic drawing showing the embodiment in FIG. 6A while injecting solution according to the present invention.

Refer to FIG. 6B, push the injection rod 66 so that the piston 662 moves and the solution 68 flows out of the hole 622 over the hole film 632. Thus while using the sampling device for vaginal specimens 60, firstly insert the tubular unit 62 into the vagina. Then push the injection rod 66 for injecting the solution into the vagina through the hole 622 as the vaginal lubricant. Thus the vaginal discomfort of women caused by the sampling unit 64 during sampling processes can be prevented.

In summary, a sampling device for vaginal specimens of the present invention includes a tubular unit and a sampling unit. The tubular unit is connected with a saclike body or is inserted with an injection rod for injecting solution into the vagina so as to lubricate the vagina and increase accuracy of the sampling.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A sampling device for vaginal specimens comprising:
a tubular unit whose front end is disposed with at least one hole and a flow channel is mounted in the tubular unit while the flow channel is connected with the hole, said at least one hole disposed on a side wall of the front end of the tubular unit;
a sampling unit arranged on the front end of the tubular unit; and
a saclike body connected with a rear end of the tubular unit and having a pour opening that connects with the flow channel;

wherein the tubular unit comprises:
- a first tubular member for being disposed with the sampling unit and side walls of one end of the first tubular member is mounted with the hole, a first flow channel of the flow channel mounted in the first tubular member; and
- a second tubular member threaded with a rear end of the first tubular member, a second flow channel of the flow channel mounted in the second tubular member, the first flow channel and the second flow channel are configured to be in a staggered arrangement before in use, and the first flow channel and the second flow channel are configured to be connected with each other correspondingly while the tubular unit is rotated in use.

2. The device as claimed in claim 1, wherein a drawing string whose one end is fastened and connected with the sampling unit is arranged in the tubular unit.

3. The device as claimed in claim 1, wherein said at least one hole is covered by a film.

4. The device as claimed in claim 1, wherein at least one scraping member is disposed on surface of the sampling unit.

5. The device as claimed in claim 4, wherein said at least one scraping member is a convex surface, a protrusion or a projecting object.

6. The device as claimed in claim 1, wherein the sampling unit is an absorptive member.

7. The device as claimed in claim 1, wherein a membrane or a stop valve is disposed on the pour opening or between the pour opening and the flow channel.

8. The device as claimed in claim 1, wherein the saclike body is configured to be pivoted to or threaded with the tubular unit.

9. The device as claimed in claim 1, wherein the saclike body is with hardness, support strength or elasticity.

* * * * *